United States Patent [19]

Rutherford et al.

[11] Patent Number: 4,542,162
[45] Date of Patent: Sep. 17, 1985

[54] PROCESS FOR FORMING INSECT, ANIMAL OR BIRD REPELLENT FLUID AND SOLID-CONTAINING THERMOPLASTIC FILMS AND PELLETS, USES THEREOF AND PROCESS FOR PRODUCING SAME

[75] Inventors: Howard J. Rutherford, Highlands; Donald A. Withycombe, Lincroft, both of N.J.

[73] Assignee: International Flavors & Fragrances Inc., New York, N.Y.

[21] Appl. No.: 646,019

[22] Filed: Aug. 31, 1984

Related U.S. Application Data

[63] Continuation-in-part of Ser. No. 465,313, Feb. 9, 1983, Pat. No. 4,521,541.

[51] Int. Cl.$^4$ ............................................. B29D 27/00
[52] U.S. Cl. ...................................... 521/79; 264/50; 264/211; 521/143
[58] Field of Search ................... 264/51, 211, 53, 50; 521/78, 79, 143

[56] References Cited

U.S. PATENT DOCUMENTS 4,184,099 6/1978 Lindauer et al. ............... 313/315 X Primary Examiner—Philip Anderson
Attorney, Agent, or Firm—Arthur L. Liberman

[57] ABSTRACT

Described is a process for preparing extruded insect, animal or bird repellent fluid and solid-containing thermoplastic foamed particles using chemical blowing agents or direct gas extrusion processes, uses of such foamed particles and articles produced from said foamed particles. The process described involves the use of a single screw or double screw extruder wherein the resin particles are added upstream from the insect, animal or bird repellent fluid or solid which, in turn, is added to the extruder upstream from the point of addition to the liquid or gaseous blowing agent.

6 Claims, 13 Drawing Figures

FIG.4
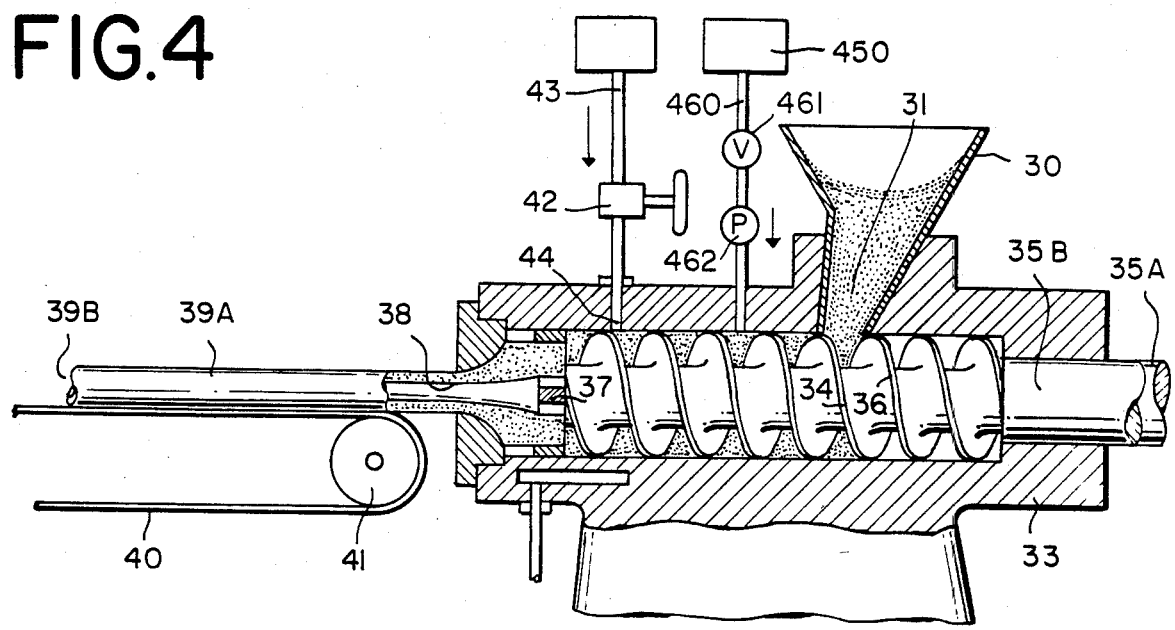
FIG.5A
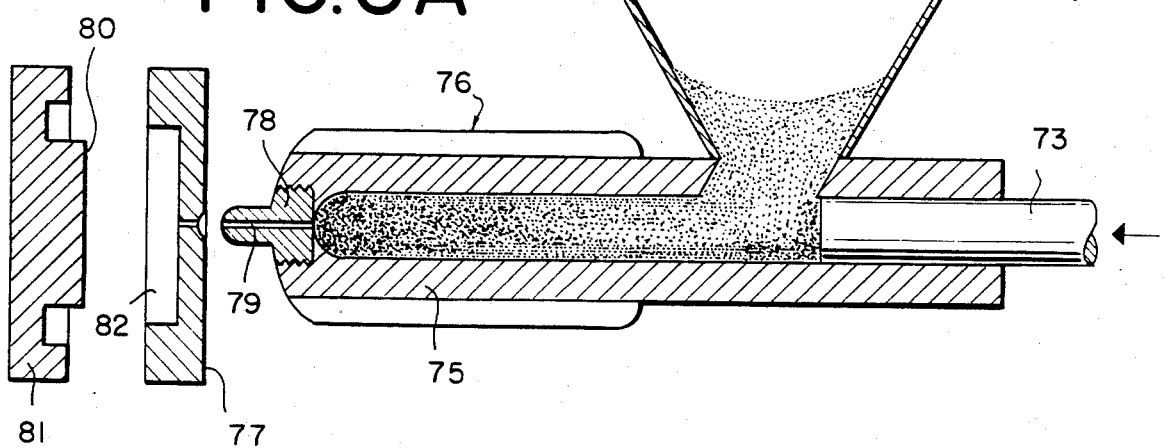
FIG.5B

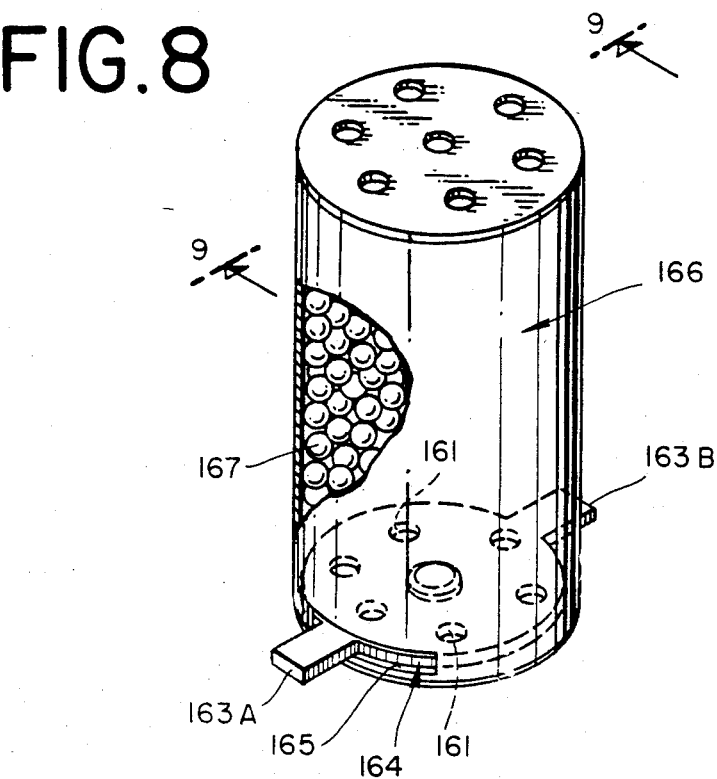
FIG. 8
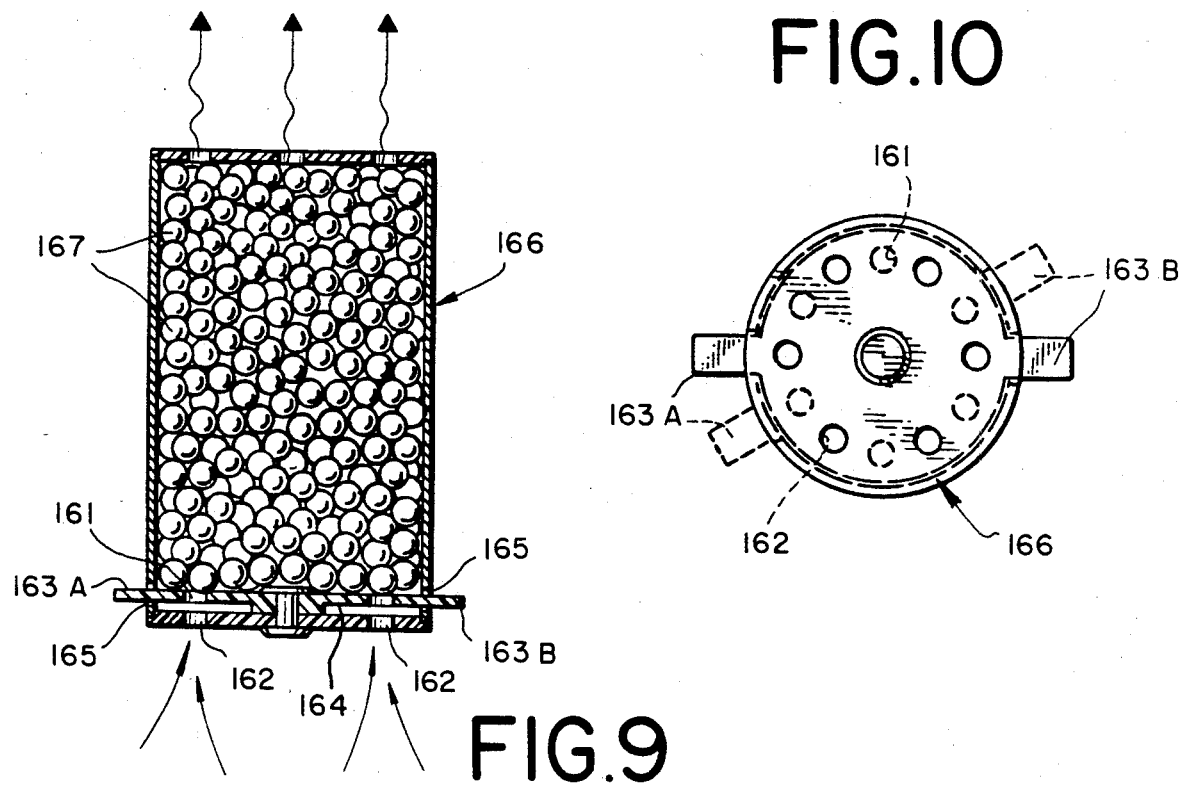
FIG. 9
FIG. 10

PROCESS FOR FORMING INSECT, ANIMAL OR BIRD REPELLENT FLUID AND SOLID-CONTAINING THERMOPLASTIC FILMS AND PELLETS, USES THEREOF AND PROCESS FOR PRODUCING SAME

This application is a continuation-in-part of application S.N. 465,313 filed on Feb. 9, 1983 now U.S. Patent No. 4,521,541.

BACKGROUND OF THE INVENTION

This invention relates to the production of and use of thermoplastic polymeric foamed particles as control release compositions for use in control release devices for controlled release of insect repellents and/or animal repellents and/or bird repellents. The process for producing such foamed particles containing such animal repellent or insect repellent or bird repellent fluids or solids involves the use of a single screw or twin screw extruder and placing the resin, animal repellent, insect repellent and/or bird repellent fluid or solid and gaseous or liquid blowing agent into the extruder stream at specific ranges of lateral intervals.

An ever increasing requirement in the animal repellent, bird repellent and insect repellent industries exists for a slow controlled release device for slowly and controllably releasing animal repellents and/or insect repellents and/or bird repellents into a gaseous environment in order to repel insects and/or in order to repel mammalian species, e.g., deer, coyote, dogs and the like and/or in order to repel birds.

Slow release polymers containing perfumes are well known in the prior art. Thus, United Kingdom Patent Specification No. 1,589,201 assigned to Hercules, Inc. discloses a thermoplastic resin body consisting of a thermoplastic polymer of ethylene and 6–60 weight percent of a polar vinyl monomer selected from the group consisting of vinyl acetate, methyl acrylate, ethyl acrylate, butyl acrylate and acrylic acid wherein the perfumed resin body is suitable for the preparation of shaped objects from which perfume odor emanates over a prolonged period at a stable level.

U.S. Pat. No. 3,505,432 discloses a method of scenting a polyolefin which comprises:
(a) mixing a first amount of liquid polyolefin, e.g. polyethylene or polypropylene with a relatively large amount of scent-imparting material to form a flowable mass;
(b) forming drops from said mass and causing substantially instantaneous solidification of said drops into polyolefin pellets having a relatively large amount of scent-imparting material imprisoned therein;
(c) melting said pellets with a second amount of said polyolefin, said second amount being larger than said first amount; and
(d) solidifying the melt of (c).

U.S. Pat. No. 4,247,498 issued on Jan. 27, 1981 discloses microporous polymers which are capable of containing volatile substances such as perfumes and the like in forms ranging from films to blocks in intricate shapes from synthetic thermoplastic polymers such as olefinic, condensation or oxidation polymers. In one embodiment of U.S. Pat. No. 4,247,498 the microporous polymers are characterized by relatively homogeneous three-dimensional cellular structure having cells connected by pores of smaller dimension. Also disclosed in U.S. Pat. No. 4,247,498 is a process for making microporous polymers from such thermoplastic polymers by heating a mixture of the polymer and a compatible liquid (e.g., a perfume substance or the like) to form a homogeneous solution, cooling said solution under non-equilibrium thermodynamic conditions to initiate liquid-liquid phase separation, and continuing said cooling until the mixture achieves substantial handling strength. Also disclosed in said U.S. Pat. No. 4,247,498 are microporous polymer products which contain relatively large amounts of such functionally useful fluids as perfume compositions and behave as solids.

U.S. Pat. No. 4,156,067 issued on May 22, 1979 discloses polyurethane polymers characterized by a molecular weight of above 6,000 and having lactone groups and hydroxyl groups in the polymer backbone being prepared by reacting a mixture of polyols, a polyfunctional lactone (e.g. epsilon caprolactone) and a polyfunctional isocyanate proportioned so as to provide certain desired polymer properties. It is indicated in said U.S. Pat. No. 4,156,067 that the product is soluble in alkaline solutions and may be used for light sensitive photographic layers on films, paper or glass; in drug delivery systems, as burn dressings, in body implants such as vascular prosthesis, in molding compositions, and in the manufacture of catheters as well as in delivery of perfume compositions in a slow release manner. It is further indicated in said U.S. Pat. No. 4,156,067 that the water absorptivity of the polyurethane/lactone polymers is above 10%, preferably in the range of about 20% to 60%, and these polymers may range in their physical properties from rigid solids to completely gellike high water absorptive polymers. It is further indicated in said U.S. Pat. No. 4,156,067 that the polymers provide a leachable substrate wherein the leaching agent may be water, gases, alcohols, esters and body fluids, e.g. animal or human.

Extrusion of thermoplastic foams is well known in the prior art. Thus, the Modern Plastics Encyclopedia (published by the McGraw-Hill Publishing Company) 1982–1983 edition at pages 274 and 275 discloses a section authored by Fred Schrafft entitled "Extruding Thermoplastic Foams". Said article on pages 274 and 275 is incorporated herein by reference. It is indicated therein that three different processes are used for the extrusion of thermoplastic foams:
(i) extrusion of expandable beads
(ii) extrusion of thermoplastics containing a chemical blowing agent and
(iii) direct gas extrusion process.

It is further indicated in the Schrafft article that the extrusion using a chemical blowing agent may be carried out on a normal single screw extruder and the direct gas extrusion process may be carried out on single and twin screw extruders. It is further indicated in the Schrafft article that common blowing agents used in the process are hydrocarbons such as pentene or fluorocarbons such as 11, 12 and 114. It is further stated that:

"the amount of blowing agent can vary widely depending on the resin and the type of product desired. However, generally about 7% blowing agent produces a product of about 5.6 lbs/cu. ft. while 18% blowing agent produces a product of about 1.9 lbs/cu. ft. ..."

U.S. Pat. No. 3,755,208 (the specification for which is incorporated by reference herein) discloses a process for avoidance of cell collapse in an extrusion process for a copolymer based on a low molecular weight alpha olefin and polar vinyl monomer whereby there is incorporated into the polymer a small amount of partial ester of a long chain fatty acid and a polyol. Federal Republic of Germany Pat. No. 1,520,790 discloses expandable polystyrene beads incorporating polyethylene or polypropylene whereby the expandable polystyrene beads are prepared by aqueous suspension polymerization of styrene with the addition of a vaporizable blowing agent, the polymerization being carried out in the presence of from 0.01 up to 1.0 weight percent polyethylene or polypropylene having a molecular weight of less than 4,000. The publication date of this German patent is May 30, 1973.

Foamable styrene polymers are indicated to be prepared according to U.S. Pat. No. 3,758,425, the disclosure of which is incorporated by reference herein. In U.S. Pat. No. 3,758,425 a process is disclosed for preparing foamable styrene polymer beads containing blowing agents with a particularly favorable narrow grain size distribution, the process comprising the use of copolymers of N-vinyl-N-alkyl acetamide having from 1 to 4 carbon atoms in the alkyl group with an ester of acrylic, methacrylic, maleic or fumaric acid with an aliphatic alcohol having a linear or branched chain and containing from 6 to 18 carbon atoms, as protective colloid in the homo- or copolymerization of styrene in an aqueous suspension in the presence of a blowing agent.

U.S. Pat. No. 3,759,641, the disclosure of which is incorporated by reference herein, as well as U.S. Pat. No. 3,577,360, the disclosure of which is incorporated by reference herein, discloses a process and apparatus for pre-expanding polymer particles to a predetermined density which particles are subject to further expansion. Thus, there is disclosed agitated particulate expandable polymer which is heated in a dry atmosphere in a closed vessel, under vacuum, to a predetermined density. To achieve ultra-low density expandable prepuff, a coolant such as water is introduced into the closed vessel after the predetermined density is reached, but prior to the release of the vacuum. Following release of the vacuum, the beads are removed from the closed vessel and may be molded directly without any aging period such as that necessary following steam pre-expansion.

German Pat. No. 1629296 published on Feb. 20, 1973, the disclosure for which is incorporated by reference herein, discloses the production of particles of foam polyethylene by exposure to an inert gas whereby the density is reduced. Thus, particles of closed cell film polyethylene are obtained by extruding an ethylene polymer in the presence of a foaming agent, e.g. isobutane. After extrusion, the product is exposed to an inert gas under high pressure at up to 20° C. below the melting point of the polymer. The inert gas has a permeability coefficient equal to or less than that of air.

U.S. Pat. No. 3,067,147 issued on Dec. 4, 1962 (Rubens, et al) assigned to Dow Chemical Company discloses the use of 1,2-dichlorotetrafluoroethane which can be injected into polyethylene during extrusion to produce an extruded gel which spontaneously expands as it is extruded into a reduced pressure. A special technique, such as cooling, has been used to produce a stable polyethylene foam as disclosed in said U.S. Pat. No. 3,067,147, the specification for which is incorporated by reference herein. The Rubens, et al patent describes an extrusion process for producing low density (0.04 grams/cm$^3$) polyethylene foams. The variables that influence the mechanical properties of these materials are disclosed in Rubens and Skochdopole in J. Cellular Plastics, January 1965 at pages 91–96, the disclosure of which is incorporated herein by reference.

As disclosed at page 269 of the text "Plastic Foams: the physics and chemistry of product performance and process technology", Volume 1: Chemistry and Physics of Foam Formation, author: Calvin J. Benning published by Wiley-Interscience, a division of John Wiley and Sons, New York, (copy in U.S. Patent and Trademark Office Scientific Library), a process for continuous extrusion of expansion of medium density (20–30 lbs. per cu. ft.) polyethylene and sheet has been commercialized by the Nippon Art Paper Company of Japan. The process consists of three steps:

1. preparing pellets impregnated with a foaming agent in solution;
2. feeding the coated pellets into the extruder;
3. extruding into the desired shape.

The key to the development of the Nippon Art Paper Company process is the use of polyethylene "expandable" pellets which can be converted into film or sheet on standard polyethylene blown-film equipment. The pellets can also be blow-molded into bottles or tubes. It is further indicated in the Benning textbook that polyethylene foamed sheet has entered such markets as greenhouse insulation, tablecloths, bags, synthetic leather, wallpaper, tents, toys and packaging.

Other "ethafoam" patents whereby expanded extruded foamed polyethylene having a cell size of 0.5–1.0 mm are indicated to be produced are set forth in Rubens, et al. U.S. Pat. No. 2,948,664 and Rubens, et al. U.S. Pat. No. 2,948,665, the disclosures for which are incorporated by reference herein.

Additional details concerning methods for producing various foams of various dimensions in various polymers are set forth in Benning "Plastic Foams: the physics and chemistry of product performance and process technology/Volume II: Structure Properties, and Applications", author: Calvin J. Benning, Wiley-Interscience a division of John Wiley and Sons, New York, copyright 1969 (copy available in United States Patent & Trademark Office scientific library), the disclosure of which is incorporated by reference herein. Of particular importance are the following pages in the Benning texts:

Volume I: pages 261–344 inclusive
Volume II: pages 20–25, 80–85, 90–93.

U.S. Pat. No. 2,860,377 issued on Nov. 18, 1958 (Bernhardt and Whitfield) discloses the production of a foamed polyethylene by dissolving a gas such as nitrogen therein at elevated pressure while the said plastic is being advanced through an extruder barrel by the action of a rotating extrusion screw, and thereafter releasing the plastic through a die whereby a plastic foam is produced.

In U.K. Patent Specification No. 1,044,397 published on Sept. 28, 1966, it is disclosed that as blowing agents for making foamed polyolefins, it is possible to employ all conventional inorganic and organic compounds which evolve a blowing gas, e.g. nitrogen or carbon dioxide, and it is further disclosed that the polyolefins to be foamed according to the invention have blowing agents which are known per se and optionally, dyestuffs and/or pigments incorporated therein.

Nothing in the prior art, however, discloses the advantages of the simultaneous foamed pellet/insect repellent and/or animal repellent and/or bird repellent fluid or solid imparting of the process of our invention.

BRIEF DESCRIPTION OF THE DRAWINGS

FIG. 4 is a cut-away side elevation view of extrusion apparatus used for extruding thermoplastic polymeric foamed tubing containing within the walls of the tubing animal repellent, bird repellent or insect repellent fluid or solid.

FIGS. 5A and 5B represent cut-away side elevation views of injection molding apparatus prior to and during the injection molding operation for the injection molding of the animal repellent, bird repellent or insect repellent fluid or solid-containing foamed polymeric pellets produced according to the process of our invention.

FIG. 5A shows the apparatus immediately prior to the carrying out of the injection molding process and FIG. 5B shows the apparatus during the injection molding process wherein the polymeric foamed pellets are being fused and pushed through the injection molding apparatus orifice into the mold.

FIG. 8 is a partially cut-away perspective view of an article of manufacture useful in the operation of the apparatus of FIG. 11 containing foamed polymeric particles containing animal repellent, bird repellent and/or insect repellent fluid or solids produced using the apparatus of FIG. 2, for example, said polymeric particles containing an animal repellent, bird repellent and/or insect repellent fluid or solid.

FIG. 9 is a cut-away side elevation view of the article of manufacture of FIG. 8 looking in the direction of the arrows.

FIG. 10 is a top view of the article of manufacture of FIG. 8.

SUMMARY OF THE INVENTION

Figure 1A:
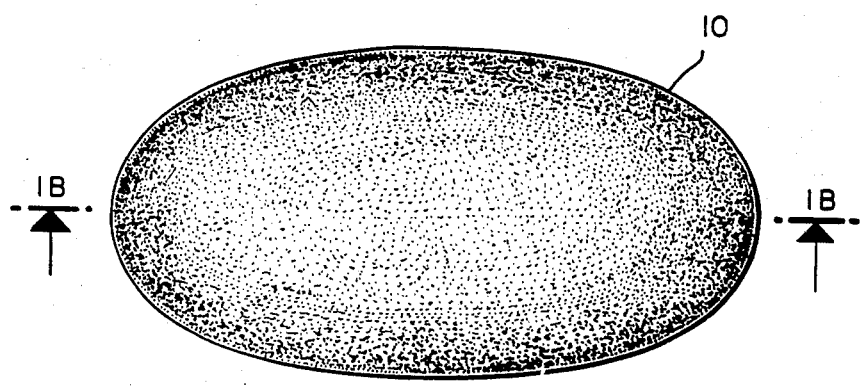
FIG. 1A represents a perspective view of the outside of a foamed polymeric particle containing animal repellent, bird repellent or insect repellent fluid or solid produced according to the process of Example I wherein a nitrogen foaming agent and an animal repellent, bird repellent or insect repellent agent were added to an extruder during the extrusion of polyethylene.

Our invention relates to the formation of foamed animal repellent, bird repellent or insect repellent fluid or solid-containing polymeric pellets by means of introduction into a single screw or twin screw extruder of, in series, thermoplastic polymer followed by animal repellent, bird repellent or insect repellent fluid or solid which is compatible with a thermoplastic polymer, in turn, followed by introduction of a gaseous blowing agent or blowing agent which will produce a gas which is inert to the polymer and to the animal repellent, bird repellent or insect repellent fluid or solid previously introduced into the extruder.

The advantages of using the foamed polymeric particles are multiple, to wit: improved handling; greater retention of animal repellent, bird repellent or insect repellent fluid or solid when not in use; greater length of time during which release of animal repellent, bird repellent or insect repellent fluid or solid from polymer is at "steady state" or "zero order".

The nature of the extruder utilized in the process of our invention to form the foamed polymeric animal repellent, bird repellent or insect repellent fluid or solid containing polymer particles of our invention may be either single screw or double screw. Thus, the types of extruders that can be used are disclosed at pages 246–267 and 332–349 of the Modern Plastics Encyclopedia, 1982–1983 published by the McGraw-Hill Publishing Company, the disclosure of which is incorporated by reference herein. More specifically, examples of extruders which are usable in carrying out the process of our invention (with modification for introduction of animal repellent, bird repellent or insect repellent fluid or solid downstream from introduction of the polymer and with a further modification that the gaseous blowing agent is introduced still further downstream from the point of introduction of the functional fluid or solid are as follows:

1. The Welex "Super Twinch" 3.5" extruder manufactured by Welex Incorporated, 850 Jolly Road, Blue Bell, Pa. 19422
2. Krauss-Maffei twin screw extruder manufactured by the Krauss-Maffei Corporation/Extruder Division, 3629 West 30th Street South, Wichita, Kans. 67277
3. Modified Sterling model 4000 and 5000 series extruder manufactured by Sterling Extruder Corporation of 901 Durham Avenue, South Plainfield, N.J.
4. CRT ("Counter-Rotating Tangential") Twin Screw Extruder manufactured by Welding Engineers, Inc. of King of Prussia, Pa. 19406
5. The Leistritz Twin Screw Dispersion Compounder manufactured by the American Leistritz Extruder Corporation of 198 U.S. Route 206 South, Somerville, N.J. 08876

6. The ZSK Twin Screw Co-Rotating Extruder manufactured by the Werner & Pfleiderer Corporation of 663 East Crescent Avenue, Ramsey, N.J. 07446
7. The Farrel Extruder manufactured by Farrel Connecticut Division, Emhart Machinery Group, Ansonia, Conn. 06401
8. The MPC/V Baker Perkins Twin Screw Extruder manufactured by the Baker Perkins Inc. Chemical Machinery Division of Saginaw, Mich. 48601
9. The Berstorff single screw, twin screw, or foam extrusion equipment manufactured by Berstorff Corporation, P.O. Box 240357, 8200-A Arrowridge Blvd., Charlotte, N.C. 28224

In producing the foamed animal repellent, bird repellent or insect repellent fluid or solid-containing polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX®" and by the Arco Polymer Division under the trademark "DYLAND®" and by the Exxon Corporation of Linden, N.J. under the trademark "DEXXON®". Ethylene/ethyl acrylate co-polymers are marketed by Union Carbide Corporation under the tradename "EEA RESINS®".

The polymer is added to the single screw or twin screw extruder at a feed rate in the range of from about 80 up to about 300 pounds per hour while maintaining the temperature in the screw extruder between about 160° and about 240° C. If the polymer or co-polymer powder is added to the extruder at a reference "barrel segment", then the animal repellent, bird repellent or insect repellent fluid or solid is added to the extruder under pressure downstream from the addition point of the polymer at 1 or more of "barrel segments" 2-9.

Thus, the invention provides a process for forming animal repellent, bird repellent and/or insect repellent fluid or solid containing foamed polymeric particles such as foamed polymeric pellets which include a relatively high concentration of a material having at least one of the functions: an animal repellent, a bird repellent or an insect repellent. The animal repellent, bird repellent or insect repellent fluid or solid added at "barrel segments" 2-9 of the single screw or twin screw extruder then has (have) one or more of the foregoing functions. Furthermore, the animal repellent, bird repellent or insect repellent fluid or solid added at "barrel segments" 2-9 must be previously or made to be compatible with the polymer added at "barrel segment" 1 of the single screw or twin screw extruder.

More specifically, the animal repellent, bird repellent, or insect repellent suitable for our invention includes substantially any of the conventional animal repellent, bird repellent or insect repellent materials as, for example, those set forth in the specifications of U.S. Pat. Nos. 3,474,176; 4,451,460; 4,449,987 or 2,967,128 the specifications of which are incorporated by reference herein.

The use as to type and proportion of animal repellent, bird repellent or insect repellent is limited only by either (a) their solubility in the resin or mixture of resins used and/or (b) the volume ratio of microvoids in the polymer to said polymer and/or (c) the solubility of the animal repellent, bird repellent or insect repellent in the polymer on solidification. the proportion of animal repellent, bird repellent or insect repellent can in many instances go up to 45% by weight.

Thus, the proportion of animal repellent, bird repellent or insect repellent fluid or solid to resin, accordingly, can vary from small but effective amounts on the order of about 1% of the weight of the resin body up to about 45% by weight of the resin body. In general, it is preferred to use between about 5% up to about 30% based on the weight of the resin body of animal repellent, bird repellent or insect repellent fluid or solid. This is an optimum amount balancing the proportion of animal repellent, bird repellent or insect repellent fluid or solid, in the product against the time period over which the article emits the animal repellent, bird repellent or insect repellent fluid or solid and against the tendency of the animal repellent bird repellent or insect repellent fluid or solid to "oil out". This "oiling out" is specifically avoided as a result of the use of the foaming agent discussed infra.

Examples of animal repellents useful as functional fluids or solids in conjunction with all aspects of our invention are set forth in U.S. Pat. No. 3,474,176 issued on Oct. 21, 1969 and U.S. Pat. No. 4,451,460 issued on May 29, 1984, the specifications for which are incorporated by reference herein. In this respect, our invention provides safe, effective compositions for controlling mammalian species whereby the materials can be in the form of sheets or strips of polymer containing the animal repellent tied about trees, plants and the like.

Briefly, for example, the animal repellents useful in our invention comprise a suitable carrier compatible with the resins, e.g., polyethylenes or polypropylenes and, if desired, copolymers admixed therewith and an aliphatic or alicyclic ketone, for example, containing from about 6 to 20 carbon atoms. The ketones are present in the composition in amounts effective to repel animals from the area in which the polymeric sheet is placed. The method of our invention comprises placing such a polymeric sheet containing an aliphatic or alicyclic ketone having from about 6 up to about 20 carbon atoms in the area where the mammalian species roams. The effective repellent substances are ketones which contain preferably from about 7 up to about 19 carbon atoms. The ketones can be saturated or unsaturated, aliphatic or alicyclic materials. The ketones desirably used in our invention are exemplified by ethylbutyl ketone, methylisoamyl ketone, geranyl acetone, ethyl-n-amyl ketone, methyloctyl ketone, heptylidene acetone, isobutylheptyl ketone, methylundecyl ketone, methylhexyl ketone and 2-methyl-6-heptanone. Preferred ketones are ethylbutyl ketone, methylisoamyl ketone and 4-t-amylcyclohexanone.

Further, for example, the animal repellents useful in our invention comprise a suitable carrier compatible with the resins, e.g., polyethylenes or polypropylenes and, if desired, co-polymers admixed therewith and one or more natural or synthetic steroids of the type occurring on human skin or hair or in human sweat or urine as well as derivatives of these steroids obtainable by subjecting the steroids to air, moisture or micro organisms. These steroids as disclosed in U.S. Pat. No. 4,451,460 are preferably:
- testosterone
- androsterone
- dehydroepiandrosterone
- 11-ketoaetiocholanalone
- i-androstanalone
- oestrone; and
- androstenol.

In place of, or in addition to, the animal repellents set forth supra, bird repellents can be used in a similar manner with our invention with the polymer composition of our invention in formulating the foamed polymeric particles of our invention. Such bird repellents are set forth in U.S. Pat. No. 2,967,128 issued on Jan. 3, 1961, the specification for which is incorporated by reference herein. As used herein "birds" are members of the class "Aves". Birds both domestic and wild such as chickens, turkeys, ducks, pheasants, crows, etc. cause much damage from an economic standpoint by eating newly planted seeds, ripening grain crops, stored corn, berries, fruits, etc.

Our invention thus utilizes esters of anthranilic acids, esters of phenyl acetic acid and dimethyl benzyl carbinol acetate as bird repellents which are compatible with the polymers which we use in forming the foamed bird repellent fluid or solid-containing polymeric particles of our invention.

Thus, esters useful in conjunction with our invention are esters of phenyl acetic acid and include such wide varieties of ester moieties as alkyl, alkenyl, aryl, aralkyl and the like. The alkyl phenyl acetates specifically exemplified are methyl phenyl acetate, ethyl phenyl acetate and isobutyl phenyl acetate. Insofar as the anthranilates are concerned as bird repellents, the optimum preferred ester for use in conjunction with the polymers used in conjunction with our invention is dimethyl anthranilate (methyl ortho-N-methylaminobenzoate). Other anthranilates or ethyl anthranilates are phenyl ethyl anthranilate, methyl anthranilate and menthyl anthranilate.

In place of and in addition to the bird repellents set forth, supra, insect repellents can be used in a similar manner with our invention with the polymer composition of our invention in formulating the foam polymeric particles of our invention. Such insect repellents are set forth in U.S. Pat. No. 4,449,987 issued on May 22, 1984, the specification for which is incorporated by reference herein. Examples of such insect repellents are those which contain:
  (i) from 1-30 parts by weight of a methyl heptenone;
  (ii) from 1-10 parts by weight of Coumarin;
  (iii) from 0.4 up to 15 parts by weight of Indole
taken alone or taken further together with a perfume composition which is substantially inactive from an insect repellent standpoint or which may be active from an insect repellent standpoint. As an example, the following composition may be used:

| Ingredients | Parts by Weight |
|---|---|
| (A) 50% by Weight of the following mixture: | |
| L-Citronella | 24.0 |
| Geraniol | 22.0 |
| Nerol | 8.0 |
| Phenylethyl alcohol | 3.0 |
| Geranyl formate | 3.5 |
| Geranyl acetate | 3.8 |
| Eugenol | 1.5 |
| Alpha Farnésene | 3.5 |
| Beta Farnesene | 4.4 |
| Citral | 4.2 |
| n-Nonanal | 4.0 |
| n-Octanal | 3.8 |
| Trans-trans-delta-damascone | 0.8 |
| and | |
| (B) One of: | |
| (i) 50% by Weight of the following mixture: | |
| 2-methyl-3-hepten-6-one | 19.0 |
| Coumarin | 3.3 |
| Indole | 0.3 |
| (ii) 50% by Weight of 2-Methyl-3-Hepten-6-one; or | |
| (iii) 50% by Weight of Coumarin. | |

As stated supra, various polymers are useful in the practice of our invention. Specific examples of polymers useful in the practice of our invention are as follows:

(a) DYLAN ® brand of low density polyethylene (DYLAN ® is a trademark owned by the Atlantic Richfield Company of Los Angeles, Calif.

(b) DYLITE ® brand of expandable polystyrene compositions. DYLITE ® is a trademark of the Atlantic Richfield Company of Los Angeles, Calif.

(c) SUPER DYLAN ® brand of high density polyethylene. SUPER DYLAN ® is a trademark of the Atlantic Richfield Company of Los Angeles, Calif.

(d) Blended polyethylene and carbon black as specifically taught in U.S. Pat. No. 4,369,267 issued on Jan. 18, 1983, the specification for which is incorporated by reference herein.

(e) Polystyrene as disclosed in U.S. Pat. No. 4,369,227 issued on Jan. 18, 1983, the specification for which is incorporated by reference herein.

(f) Polyene/alpha-olefin copolymers as exemplified and disclosed in U.S. Pat. No. 4,369,291, the specification for which is incorporated by reference herein.

(g) Poly-alpha-olefins as exemplified in Canadian Pat. No. 1,137,069 issued on Dec. 7, 1982, the specification for which is incorporated by reference herein.

(h) Polymeric compositions as disclosed in Canadian Pat. No. 1,137,068 issued on Dec. 7, 1982, the specification for which is incorporated by reference herein.

(i) Poly-alpha-olefins disclosed in Canadian Pat. No. 1,137,067, the specification for which is incorporated by reference herein.

(j) Polyolefins described in Canadian Pat. No. 1,137,066, the specification for which is incorporated by reference herein.

(k) Polyethylene oxides as disclosed in Canadian Pat. No. 1,137,065 issued on Dec. 7, 1982, the specification for which is incorporated by reference herein.

(l) Olefin polymers and co-polymers as disclosed in Canadian Pat. No. 1,139,737, the disclosure of which is incorporated by reference herein. Canadian Pat. No. 1,139,737 was issued on Jan. 18, 1983.

(m) Polyolefins disclosed in Canadian Pat. No. 1,139,738, the specification for which is incorporated by reference herein. Canadian Pat. No. 1,139,738 was issued on Jan. 18, 1983.

(n) Chlorinated PVC as disclosed in Polymer 1982, 23 (7, Suppl.), 1051-6 abstracted at Chem. Abstracts 97:145570y, 1982.

(o) Polyepsilon caprolactone co-polymers made by means of alcohol initiated polymerization as disclosed in *J. Polym. Sci.* Polym. Chem. Ed. 1982, 20(2), pages 319-26, abstracted at Chem. Abstracts, Volume 96: 123625x, 1982.

(p) Styrene acrylonitrile co-polymers as disclosed in Diss. Abstracts, Int. B, 1982, 42(8), 3346 and abstracted at Chem. Abstracts 96:143750n (1982).

(q) Co-polymers of epsilon caprolactone with 1,4-butane diol as disclosed at Kauch. Rezine, 1982, (2), 8-9, abstracted at Chem. Abstracts, Volume 96:182506g (1982).

(r) Polyesters as disclosed in U.S. Pat. No. 4,326,010, the specification for which is incorporated by reference herein.

(s) Chlorinated polyethylene as disclosed by Belorgey, et al. *J. Polym. Sci.* Polym. Phys. Ed. 1982, 20(2), 191-203.

(t) Plasticized polyepsilon caprolactone co-polymers containing dimethyl phthalate plasticizers as set forth in Japanese Pat. No. J81/147844, abstracted at Chem. Ahstracts, Volume 96:69984y (1982), the specification for which is incorporated by reference herein.

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein.

(v) Polyurethane polymers having lactone backbones as disclosed in U.S. Pat. No. 4,156,067 issued on May 22, 1979, the disclosure of which is incorporated by reference herein.

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein.

(x) Resins having polyurethane backbones as disclosed in U.S. Pat. No. 3,975,350 issued on Aug. 17, 1976, the disclosure of which is incorporated by reference herein.

Downstream from the addition point of the animal repellent, bird repellent or insect repellent fluid of solid in the extruder, the gaseous or liquid containing blowing agent may be added (e.g., segment as a reference barrel segment "1". Examples of gaseous at "barrel segments" 5-10, using the polymer addition barrel blowing agents are carbon dioxide, nitrogen, mixtures of nitrogen and carbon dioxide in proportions from 1 up to 99% by volume nitrogen and 99% down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of the addition may vary from about 80 up to about 150 psig. Higher pressures may be used without adversely affecting the usefulness of the foamed animal repellent, bird repellent or insect repellent fluid or solid-containing polymer particle.

The feed rate range of animal repellent, bird repellent or insect repellent fluid or solid may be between about 0.5% up to about 45% by weight of the polymer.

The die of the extruder may create rod, sheet, film or ribbon. The resulting product may them, if desired, be pelletized to form foamed animal repellent, bird repellent or insect repellent fluid or solid-containing polymer particles or the ribbon may be used as is as a foamed animal repellent, bird repellent or insect repellent fluid or solid-containing polymeric article of manufacture itself.

In addition to the gaseous blowing agents (which are necessarily "inert" gases), blowing agents may be added at the same point on the extruder which will create gaseous voids in the animal repellent, bird repellent or insect repellent fluid or solid-containing polymeric articles of our invention and these "blowing agents" are well known to one having ordinary skill in the art. Examples of such non-gaseous containing materials which yield gases on admixture with the polymer in the extruder but which are still inert to the animal repellent, bird repellent or insect repellent fluid or solid are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein.

(ii) Ordinarily liquid materials such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1-5, the specification for which is incorporated by reference herein.

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference.

(iv) Azo bis(formamide); diazoaminobenzene; N,N'-dinitrosopentamethylene tetramine; N,N'-dimethyl-N,N'-dinitrosoterephthalamide; p,p'-xy-bis(benzene sulfonyl semicarbazide); azo bis(isobutyronitrile); p,p'-oxy-bis(benzene sulfonyl hydrazide); p,p'-diphenyl-bis (sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be for example injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

FIG. 1A is an outer view of a foamed polymeric particle containing functional fluid or solid as indicated by reference numeral "10".

Figure 1B:
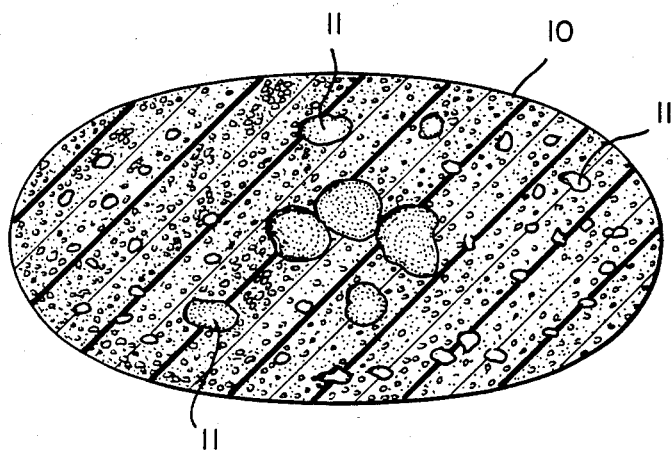
FIG. 1B is a cut-away side elevation view of the particle of FIG. 1A.

FIG. 1B is a cross-section of the particle of FIG. 1A taken along line 1B in FIG. 1A. Part of the particle indicated by reference numeral "10" is the outer surface thereof. Reference numeral "11" indicates one of the pores produced as a result of foaming.

Figure 2:
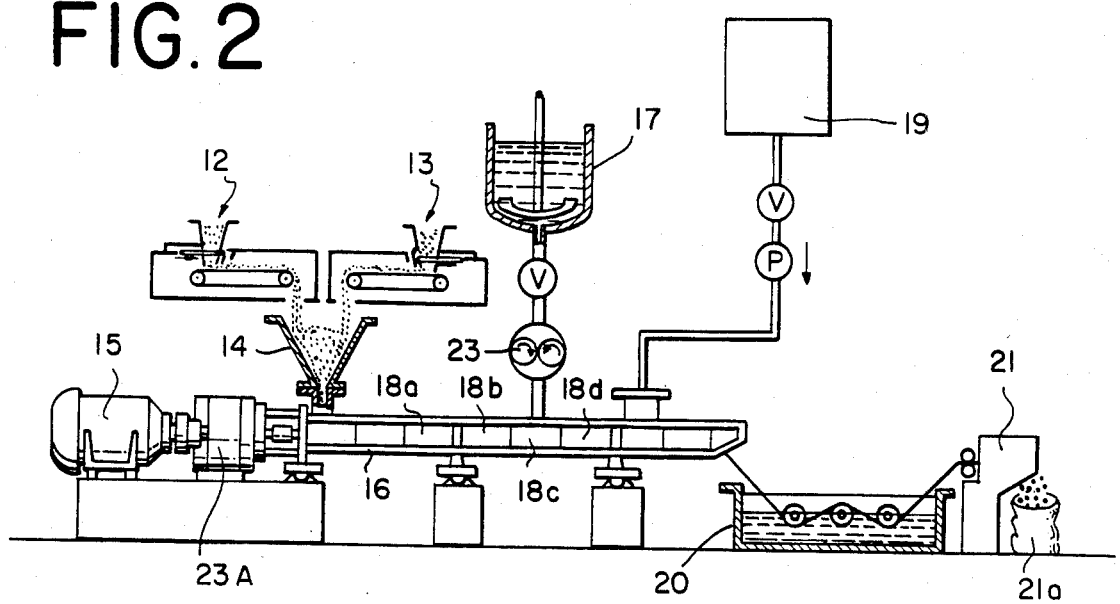
FIG. 2 is a cut-away side elevation schematic diagram of a screw extruder during the compounding of the resin with the animal repellent, bird repellent or insect repellent fluid or solid while simultaneously adding foaming agent into the hollow portion of the barrel of the extruder and incorporates the pelletizing apparatus used in pelletizing the extruded foamed tow produced as a result of the extrusion operation.

FIG. 2 is a schematic cut-away elevation diagram of the extrusion and pelletizing apparatus useful in carrying out the process of our invention during the operation of said apparatus. Motor 15 drives the extruder screws located at 23A in barrel 16, the extruder being operated at temperatures in the range of about 150° up to about 250° C. At the beginning of the barrel resin at source 12 together with additives, e.g. opacifiers, processing aids, colors, pearlescent agents and densifiers at location 13 is added via addition funnel 14 into the extruder. Simultaneously (when the operation reaches "steady state"), animal repellent, bird repellent or insect repellent fluid or solid is added to the extruder at one, two or more of barrel segments 3-8 of the extruder (which may be a twin screw or single screw extruder) at locations 18a, 18b, 18c and 18d by means of gear pump 23 from source 17. From source 19 into barrel segments 5-10, the gaseous or liquid blowing agents, e.g., nitrogen, carbon dioxide and the like as described, supra are added simultaneously with the addition of the animal repellent, bird repellent or insect repellent fluid or solid. The feed rate range of resin is about 80-300 pounds per hour. The feed rate range of the animal repellent, bird repellent or insect repellent solid or liquid is between 1 and 35% of the feed rate range of the resin. The blowing agent rate range is such that the pressure of the gas or the pressure over the liquid being fed into the extruder is between about 50 and 200 psig. If desired, the extruded ribbon or cyliner may be passed through water bath 20 and pelletizer 21 into collection apparatus 21a. FIG. 22 indicates the travel of the extruded material prior to entering pelletizer 21.

Figure 3:
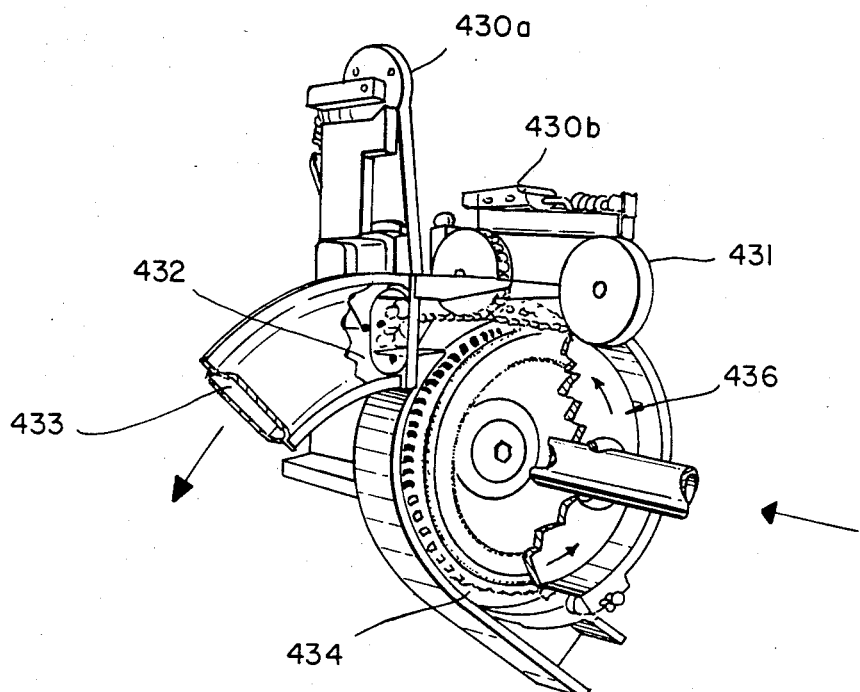
FIG. 3 is a cut-away perspective diagram of a pelletizing apparatus used in conjunction with the extrusion apparatus, for example that illustrated in FIG. 2, whereby the extruded tow is pelletized.

FIG. 3 is a detailed cut-away perspective view of such a pelletizer as is used in conjunction with the apparatus of FIG. 2. The extruded material coming from the water cooler which is already foamed and which already contains animal repellent, bird repellent or insect repellent fluid or solid is fed into the pelletizer at zero pressure at location 434. The pelletizer is operated using a spinning extrusion die 436 and operated by means of a rotating wheel 434. Moving pellet knife 431 and dual knife units 430a and 430b cause pellets to be formed which fly into a cooling water stream 432. The resulting pellets which are foamed and contain animal repellent, bird repellent or insect repellent solid or liquid exit from the pelletizer at 433.

Similarly, an extruded tube which can be used as such or cut into smaller lengths is shown to be formed using the apparatus of FIG. 4. Thus, a single screw 35B taken alone or further together with a second screw 35A makes up part of an extruder in casing 33. Resin from resin funnel 30 is fed in at location 31 into the extrusion barrel upstream from the feeding of animal repellent, bird repellent or insect repellent fluid or solid which is located at source 450. Simultaneously, animal repellent, bird repellent or insect repellent fluid or solid from source 450 is fed through line 460 past valve 461 using pump 462 into the extrusion barrel. The extruder causes an intimate mixing of the animal repellent, bird repellent or insect repellent fluid or solid with the resin in the screw conveyor threads 34 and 36. Simultaneously upstream from the addition point of the animal repellent, bird repellent or insect repellent fluid or solid, gaseous blowing agent is fed through line 43 past valve 42 into the extrusion screws at location 44. The extruded tube then is forced through die 37 and orifice 38 onto conveyor belt 40 in the form of tube 39A which may be subsequently cut at location 39B. The conveyor belt is operated using roller 41.

The resulting extruded foam tubing or foamed pellets may be cut up for the purpose of creation of an article of manufacture which contains an animal repellent, bird repellent or insect repellent fluid or solid. Such article of manufacture may be molded using injection molding apparatus of the type set forth in FIGS. 5A, 5B and 6 or jet molding apparatus of the type set forth in FIG. 7.

Figure 6:
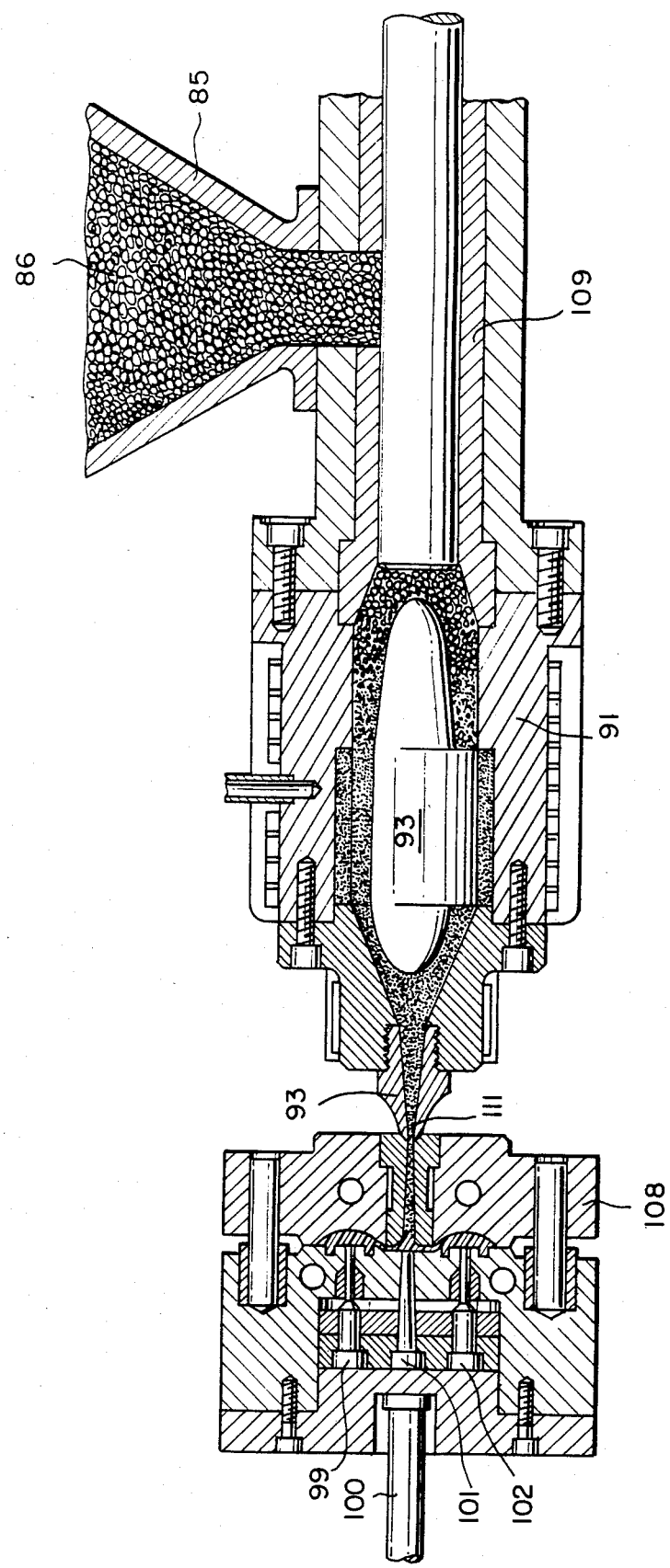
FIG. 6 is a cut-away side elevation view of injection molding apparatus useful in forming articles from the foamed polymeric pellets containing animal repellent, bird repellent or insect repellent fluid or solid produced according to the process of our invention.

FIGS. 5A and 5B show the injection molding apparatus in operation. In FIG. 5A, plunger 73 pushes the foamed animal repellent, bird repellent or insect repellent fluid or solid-containing polymeric particles through cylinder 75 heated by heating unit 76 through die 78 out of orifice 79 into the mold 77/82/80/81. The mold is composed of a male portion 80 and female portion 82. Thus, in summary, the injection molding is characterized by the fact that the molding mix is preheated in a plasticizing cyclinder having a cylinder liner 109 (as is shown in FIG. 6) to a temperature high enough for it to retain a quasi-liquid condition and is then forced by plunger 89 through the plunger cylinder into heating cylinder 91 (the temperature for which is measured using a thermocouple in thermocouple container 94), into a closed mold 108 which is cold enough to "freeze" the mixture to a solid sufficiently rigid for ejection. Molding mix containing the foamed polymeric particles 86 is fed into the plasticizing cylinder through hopper 85. When the mold opens, the cylinder plunger 89 moves back permitting material to drop into the cylinder. On the closing stroke, the mold members lock tightly together and the cylinder plunger moves forward forcing the newly delivered material from the hopper into the heating zone of the cylinder 90. This material, in turn, displaces a "shot" of molten material through the nozzle 93 into the mold cavity through orifice 111. The mold is cooled so that the shot hardens quickly. Conditions are controlled so that the molten plastic just has time to reach the outermost recesses of the mold cavity before flow ceases. When the mold is opened, the formed piece is loosened by knockout pins 99, 100 and 101 and 102. The function of the spreader 90 is to spread the mix into thin films and facilitate uniform heating as it passes toward the nozzle 93.

Figure 7:
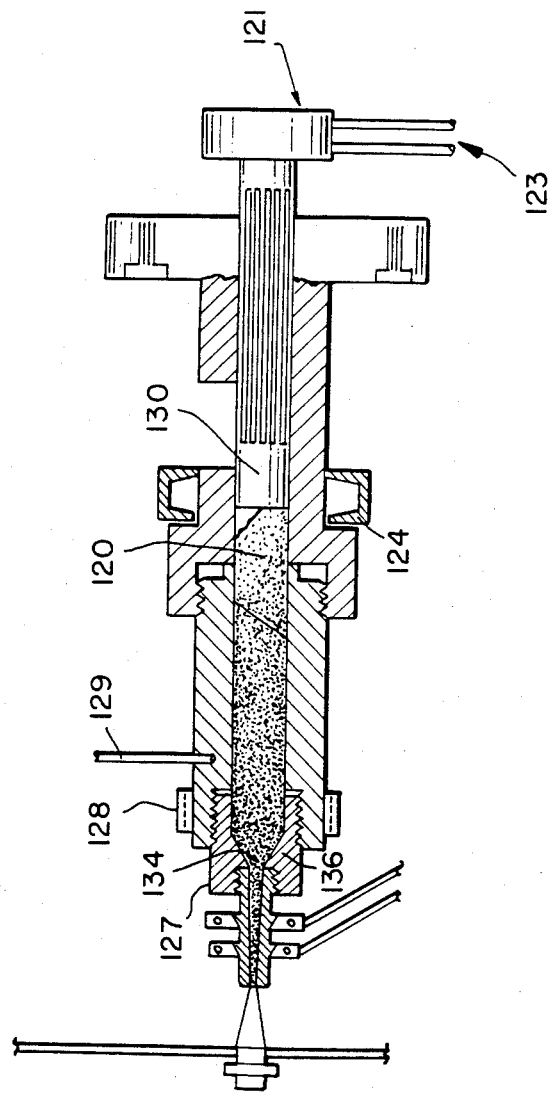
FIG. 7 is a cut-away side elevation schematic view of jet molding apparatus useful in forming articles of manufacture from the foamed polymeric pellets containing animal repellent, bird repellent or insect repellent fluid or solid produced according to the process of our invention.

In FIG. 7 which is a schematic diagram of a cut-away elevation view of a jet molding apparatus useful in producing articles of manufacture using the foamed polymeric animal repellent, bird repellent or insect repellent fluid or solid-containing particles of our invention, the mix 120 is fed into a hopper and from thence falls into a feed cylinder at 120 which is cooled using water cooling 124. The material is then moved forward toward the nozzle end of the cylinder consisting of a nozzle block containing a full taper 127 and heated by a band heater at 128. The amount of heat and rate of heating is measured using a controlling thermocouple 129. The pressure is supplied by the injection plunger 130 having water cooling connection 123 at location 121. As the mix nears the nozzle, mold heat is applied. Temperatures of 150°-200° F. are maintained and the mix is merely warmed in this zone. Under the high pressure of the injection plunger 130, the foamed polymeric animal repellent, bird repellent and insect repellent fluid or solid-containing particles begins to flow into the nozzle 136 at location 134. Thus, for example, placed around the nozzle are two or more electrodes by means of more electrodes by means of which intense heat is generated by induction. The heat is transferred to the thin stream of mix as it passes through the nozzle 136. By this means, the temperature of the mix is raised almost instantaneously to 400°–500° F. Too high a jet molding temperature can create a destruction of the animal repellent, bird repellent or insect repellent fluid or solid during the production of the animal repellent, bird repellent or insect repellent fluid or solid-containing article of manufacture.

Another feature of our invention is a mass flow control device which can be made into a part of an article utilizing the animal repellent, bird repellent or insect repellent fluid or solid-containing foamed polymers of our invention as is shown in FIGS. 8, 9, 10 and 11. Thus, after placing polymeric foamed functional fluid or solid-containing pellets 167 into cylinder 166 (the pellets, for example, being pellets produced using the apparatus shown in FIGS. 2 and 3), the article which includes mass flow rate accessory 164 with protrusions 163A and 163B is placed into the apparatus shown in FIG. 11 at locations 2030 on manifold 2016*a*.

Figure 11:
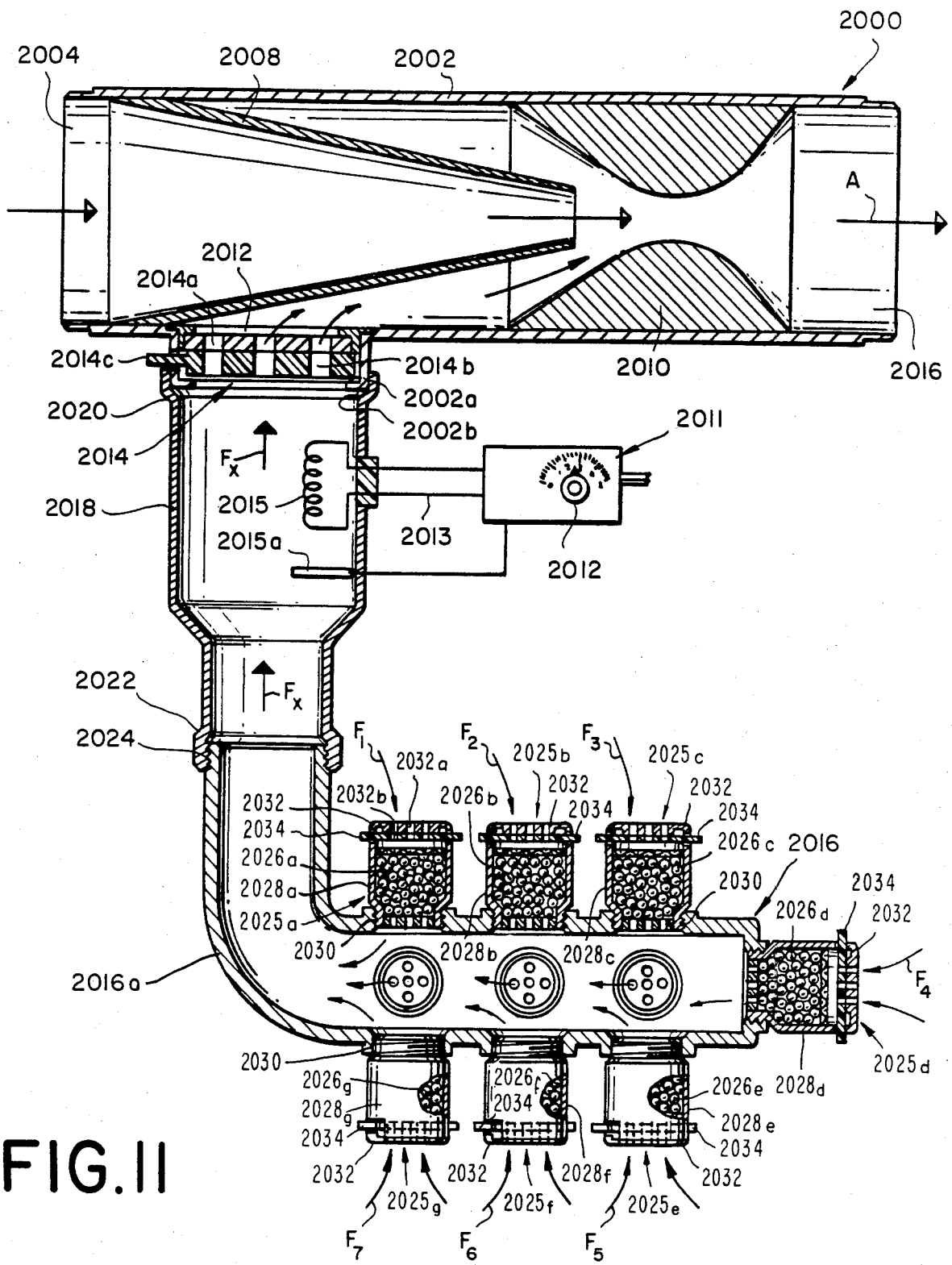
FIG. 11 is a cut-away side elevation view of a section of apparatus useful in employing the foamed polymeric particles containing animal repellent, bird repellent and/or insect repellent fluids or solids of our invention, said apparatus (i) having detachably affixed thereto a manifold which contains a multiplicity of air passageways which enables air to flow past the polymer particle surfaces and (ii) said manifold having located therein a multiplicity of detachably affixed versions of articles of manufacture containing the foamed polymeric particles which contain animal repellent, bird repellent and/or insect repellent fluids or solids of our invention.

FIG. 11 illustrates a device containing an adjustable Venturi throat resulting from the use of a nozzle having an adjustable opening used in conjunction with articles which contain the foamed polymeric animal repellent, bird repellent or insect repellent fluid or solid-containing polymers of our invention. Examples of variable Venturi throat devices are known in the prior art as set forth in U.S. Pat. No. 1,583,301, U.S. Pat. No. 4,043,772 ("Venturi Scrubber with Variable Area Throat"), U.S. Pat. No. 4,023,942 ("Variable Throat Venturi Scrubber") and U.S. Pat. No. 3,768,234 ("Venturi Scrubber System Including Control of Liquid Flow Responsive to Gas Flow Rate"), the specifications for which are incorporated by reference herein.

Referring to FIG. 11 wherein various animal repellent, bird repellent or insect repellent air treatment substances are adsorbed onto foamed polymeric particles (e.g., polyethylene or co-polymers, e.g., polyethylene-polvvinyl acetate) 2018*a*, 2018*b*, 2018*c* and 2018*d*, these substances may be desorbed in a controlled manner into manifold 2020 and thence through elbow 2016 and duct 2010 past openings 2007 and 2008 into air stream "A". This presupposes that air stream "A" is moving in the direction indicated through the nozzle 2001 past Venturi 2003 having Venturi throat 2002 contained in the main duct 2000. The multiplicity of articles of manufacture of our invention 2017*a*, 2017*b*, 2017*c*, 2017*d*, 2017*e*, 2017*f*, 2017*g*, 2017*h*, 2017*k*, 2017*m* and other articles of manufacture which may be detachably affixed at, for example, 2019*a* to manifold 2020 may be manipulated whereby air streams "$F_1$", "$F_2$", "$F_3$", "$F_4$", "$F_5$", "$F_6$" and "$F_7$", et al may be varied insofar as their mass flow rates are concerned past the foamed animal repellent, bird repellent or insect repellent solid or fluid-containing polymeric particles of our invention being indicated by reference numerals "2019*a*", "2019*b*", "2019*c*", "2019*d*" . . . "2019*m*". Each of these air streams "$F_1$", "$F_2$", "$F_3$", "$F_4$", "$F_5$", "$F_6$", "$F_7$", et seq. may be controlled by varying the variable openings 2023*a*, 2023*b*, 2023*c*, 2022*d*, et seq. using the variable opening device 2022*a*, 2022*b*, 2022*c*, et seq. In addition, the overall flow of mixed animal repellent, bird repellent and/or insect repellent gas passing through openings 2007 and 2008 may be varied using control lever 2004 whereby the openings 2007 and 2008 may be offset from "full flow" to "no flow".

Still another important feature of the utilization of the present invention is illustrated in FIG. 11 wherein a multiple manifold carrying a plurality of articles of manufacture may be used for treating the air with insect repellents and/or animal repellents and/or bird repellents is illustrated.

It will be apparent that the apparatus 2000 illustrated in FIG. 11 comprises an elongated air duct 2002 having an air inlet 2004 and an air outlet 2006. The elongated air duct 2002 includes a nozzle 2008 and a Venturi throat 2010 which constitutes the aspirating mixing system of the present invention. Furthermore, the air duct 2002 includes an opening 2012 wherein a flow control device 2014 is conveniently arranged to control the overall flow of animal repellent, bird repellent or insect repellent fluid passing therethrough.

A multiple manifold 2016 is operative by means of a connection to the elongated air duct 2002 through a duct 2018 having one end 2020 welded to a collar 2002*a* which is an integral part of the duct 2002 and provides a seat 2002*b* for the flow control device 2014. The opposite end 2022 of duct 2018 includes a male threaded portion 2024 capable of being connected to the open end of an elbow 2016*a*. It will be appreciated by one examining the above construction that elbow 2016*a* constitutes an important part of the multiple manifold 2016 since it carries a multiplicity of articles of manufacture 2025*a*, 2025*b*, 2025*c*, 2025*d*, 2025*e*, 2025*f* and 2025*g* which may be detachably affixed thereon. These articles of manufacture may contain various animal repellent, bird repellent and/or insect repellent substances imbedded into or adsorbed on the foamed polymeric functional fluid-containing particles 2026*a*, 2026*b*, . . . 2026*g* housed in cartridges 2028*a*, 2028*b*, 2028*c* . . . 2028*g* detachably connected to a threaded portion 2030 of elbow 2016. Each article of manufacture 2025*a*, 2025*b*, 2025*c* . . . 2025*g*, etc. may include an air flow control cap 2032 for controlling air streams "$F_1$", "$F_2$", "$F_3$", "$F_4$", "$F_5$", "$F_6$", "$F_7$", etc. in a controllable manner passing through each individual cartridge by varying the variable openings 2032*a* and 2032*b* of the flow control cap 2032 through a control lever 2034. Each control lever 2034 may be manipulated whereby air streams "$F_1$", "$F_2$", . . . "$F_7$", etc. may be varied insofar as their mass flow rates are concerned past the foamed polymeric particles containing animal repellent, bird repellent and/or insect repellent substances adsorbed thereon or dissolved therein.

However, the overall flow of mixed animal repellent, bird repellent and/or insect repellent gas passing into air duct 2002 to be mixed with the air stream "A" moving in the direction indicated through the nozzle 2008 and Venturi throat 2010, may be varied using the flow control device 2014 whereby opening 2014*a* and 2014*b* may be offset from full flow to no flow through a control lever 2014*c*.

The gas stream "$F_x$" which is the sum of the air streams "$F_1$", "$F_2$", "$F_3$", "$F_4$", "$F_5$", "$F_6$", "$F_7$", et seq. and the sum of the mass flow rates of animal repellent, bird repellent and/or insect repellent fluid being desorbed from foamed polymer particles 2026*a*, 2026*b*, et seq., "$F_{p1}$", "$F_{p2}$", "$F_{p3}$" et seq. is shown by the equation:

$$\Sigma[F_n+F_{pn}]=F_x$$

wherein "$F_n$" is the flow rate of the air through the articles of manufacture of our invention 2025*a*, 2025*b*, 2025c, et seq. and the flow rate of the desorbed animal repellent, bird repellent and/or insect repellent fluid from the foamed polymeric particles in the articles of manufacture of our invention "$F_{p1}$", "$F_{p2}$", "$F_{p3}$" et seq. Thus, "$F_n$" is defined according to the equation:

$$\sum_{1}^{ni} [F_1 + F_2 + \ldots + F_{ni}] = F_n$$

and "$F_{pn}$" is defined according to the equation:

$$\sum_{p1}^{pni} [F_{p1} + F_{p2} + \ldots + F_{pni}] = F_{pn}$$

The flow of the animal repellent, bird repellent and/or insect repellent fluid combined with the aspirated air "$F_1$", "$F_2$", "$F_3$", "$F_4$", "$F_5$" is shown as "$F_x$" and joins the main gas stream "A" at Venturi throat 2010 whereby the sum total of gas streams evolving at 2006 from duct 2002 is shown as "Q" or "$F_x+A$" thusly:

$$\Sigma[F_x+A]=Q$$

The temperature of stream "$F_x$" may be controlled using heating means 2011 having a control device 2012 which may be manually or automatically controlled by means of an electronic program controller. The control line 2013 is operatively connected to a heating device 2015 which may be continuous or intermittent operatively connected to a temperature sensing device 2015a which may be connected via thermostat to said heating means 2011.

What is claimed is:

1. A process for preparing a animal repellent, bird repellent and/or insect repellent containing foamed polymeric article of manufacture utilizing apparatus comprising a single screw or a twin screw extruder comprising an extruder barrel, said extruder barrel having a multiplicity of barrel segments, located within the extruder barrel, one or two parallel extruder screws, said extruder barrel having a first orifice at the location of a first extruder segment, a second orifice located at a second barrel segment at least one barrel segment downstream from said first barrel segment, and a third orifice located at a third barrel segment at least one barrel segment downstream from said second barrel segment, comprising the steps of:

(i) extruding a thermoplastic resin with a volatile bird repellent, animal repellent and/or insect repellent composition which is compatible with said thermoplastic resin, by adding said thermoplastic resin at said first orifice of said extruder and adding said bird repellent, animal repellent and/or insect repellent composition at said second orifice of said extruder, while simultaneously adding downstream from said second orifice, at said third orifice, a gaseous blowing agent selected from the group consisting of nitrogen and carbon dioxide; and (ii) then pelletizing the product so extruded, the temperature range in the extruder being from about 160° up to about 240° C.; the feed rate of the resin being from about 80 up to about 300 lbs. per hour into the extruder; the pressure of the gaseous blowing agent at said third orifice being from about 80 up to about 150 psig; the feed rate range of bird repellent, animal repellent and/or insect repellent composition at said second orifice being between 1 and 35 percent of the feed rate range of said resin; said thermoplastic resin being compatible with said bird repellent, animal repellent and/or insect repellent composition.

2. The process of claim 1 wherein the blowing agent is nitrogen.

3. The process of claim 1 wherein the blowing agent is carbon dioxide.

4. The process of claim 1 wherein the polymer being extruded is low density polyethylene.

5. The process of claim 1 wherein the polymer being extruded is high density polyethylene.

6. The product prepared according to the process of claim 1.

* * * * *